US007125664B2

(12) United States Patent
Minc-Golomb

(10) Patent No.: US 7,125,664 B2
(45) Date of Patent: Oct. 24, 2006

(54) METHOD FOR IDENTIFYING GENES THAT ARE UPSTREAM REGULATORS OF OTHER GENES OF INTEREST

(76) Inventor: Dahlia Minc-Golomb, P.O. Box 2167, 15 Simtat Hagiva Street, Savyo 56530 (IL)

( * ) Notice: Subject to any disclaimer, the term of this patent is extended or adjusted under 35 U.S.C. 154(b) by 396 days.

(21) Appl. No.: 10/175,644

(22) Filed: Jun. 20, 2002

(65) Prior Publication Data

US 2002/0197641 A1    Dec. 26, 2002

Related U.S. Application Data

(60) Provisional application No. 60/299,691, filed on Jun. 20, 2001.

(51) Int. Cl.
*C12Q 1/68* (2006.01)
(52) U.S. Cl. .......................................................... 435/6
(58) Field of Classification Search .................... 435/6; 536/24.1, 24.3, 24.31, 24.32
See application file for complete search history.

(56) References Cited

U.S. PATENT DOCUMENTS

| | | | | |
|---|---|---|---|---|
| 4,666,828 A | 5/1987 | Gusella | .......................... | 435/6 |
| 4,683,202 A | 7/1987 | Mullis | ........................ | 435/91.2 |
| 4,801,531 A | 1/1989 | Frossard | ........................ | 435/6 |
| 4,866,042 A | 9/1989 | Neuwelt | ..................... | 424/93.2 |
| 5,192,659 A | 3/1993 | Simons | ........................... | 435/6 |
| 5,272,057 A | 12/1993 | Smulson et al. | ............... | 435/6 |
| 5,464,764 A | 11/1995 | Capecchi et al. | .............. | 435/6 |
| 5,487,992 A | 1/1996 | Capecchi et al. | .............. | 435/6 |
| 6,426,185 B1 * | 7/2002 | Kumagai et al. | .............. | 435/6 |

OTHER PUBLICATIONS

USB Molecular Biology Reagents/Protocols 1992, United States Biochemical Corporation, Cleveland, Ohio, 1991, pp. 217-219.*
Minc-Golomb et al, NY Acad. Sci. 738: 462-467 (1994).*
Brummelkamp et al., "A System for Stable Expression of Short Interfering RNAs in Mammalian Cells", *Science*, 296:550-553 (2002).
Caplen et al., "Rescue of Polygultamine-Mediated Cytotoxicity by Double-Stranded RNA-Mediated RNA Interference", *Human Molecular Genetics*, 11(2):175-184 (2002).
Caplen et al., "Specific Inhibition of Gene Expression by Small Double-Stranded RNAs in Invertebrate and Vertebrate Systems", *PNAS*, 98(17):9742-9747 (2001).
Carson et al., "Simultaneous Quantitation of 15 Cytokines Using a Multiplexed Flow Cytometric Assay", *Journal of Immunological Methods*, 227:41-52 (1999).
Culver, "Correction of Chromosomal Point Mutations in Human Cells With Bifunctional Oligonucleotides", Abstract only, Antisense DNA & RNA based therapeutics, Feb. 1998, Coronado, CA.
Dharmacon Research Inc., "siRNA Oligonucleotides for RNAi Applications", Technical Bulletin #004 (2001).
Elbashir et al., "Analysis of Gene Function in Somatic Mammalian Cells Using Small Interfering RNAs", *Methods*, 26:199-213 (2002).
Elbashir et al., "Duplexes of 21-Nucleotide RNAs Mediate RNA Interference in Cultured Mammalian Cells", *Nature*, 411:494-498 (2001).
Fire et al., "Potent and Specific Genetic Interference by Double-Stranded RNA in *Caenorhabditis elegans*", *Nature*, 391:806-811 (1998).
Gavrilyuk et al., "A 27-bp Region of the Inducible Nitric Oxide Synthase Promoter Regulates Expression in Glial Cells", *Journal of Neurochemistry*, 78:129-140 (2001).
Gilboa et al., "Transfer and Expression of Cloned Gene Using Retroviral Vectors", *Bio Techniques*, 4(6):504-512 (1986).
Granucci et al., "IL-2 Mediates Adjuvant Effect of Dendritic Cells", *TRENDS in Immunology*, 23(4):169-171 (2002).
Harborth et al., "Identification of Essential Genes in Cultured Mammalian Cells Using Small Interfering RNAs", *Journal of Cell Science*, 114:4557-4565 (2001).
Huxley et al., "The Human HPRT Gene on a Yeast Artificial Chromosome is Functional When Transferred to Mouse Cells by Cell Fusion", *Genomics*, 9:742-750 (1991).
Körbling et al., "Hepatocytes and Epithelial Cells of Donor Origin in Recipients of Peripheral-Blood Stem Cells", *The New England Journal of Medicine*, 346(10):738-744 (2002).
Maeda et al., "Large-Scale Analysis of Gene Function in *Caenorhabditis elegans* by high-throughput RNAi", *Current Biology*, 11:171-176 (2001).

(Continued)

*Primary Examiner*—James Martinell
(74) *Attorney, Agent, or Firm*—Fennemore Craig, P.C.

(57) ABSTRACT

There is provided a method for identifying genes that regulate the expression of other genes, by placing a sample containing genetic material in a section of a grid, silencing expression of at least one predetermined gene in the sample, grown in the section of the grid, so that in each section of the grid at least one predetermined gene is silenced, determining the amount of genetic material of interest is present in each section of the grid, and identifying the sections of the grid in which the silencing was maximal thereby identifying genes that regulate the expression of other genes and the genes of interest identified by the method. Also provided by the present invention is a kit for performing the above method, the kit having a grid for holding a sample, inactivating agents for inactivating genetic material in the sample, and a measuring device for measuring the inactivation of the genetic material.

15 Claims, No Drawings

OTHER PUBLICATIONS

Mills et al., "DNA Microarrays and Beyond: Completing the Journey from Tissue to Cell", *Nature Cell Biology*, 3:E175-E178 (2001).

Mimics et al., "Analysis of Complex Brain Disorders with Gene Expression Microarrays: Schizophrenia as a Disease of the Synapse", *TRENDS in Neurosciences*, 24(8):479-486 (2001).

Minc-Golomb et al., "Gene Dosage of CuZnSOD and Down's Syndrome: Diminished Prostaglandin Synthesis in Human Trisomy 21, Transfected Cells and Transgenic Mice", *The EMBO Journal*, 10(8):2119-2124 (1991).

Minc-Golomb et al., "Release of D-[$^3$H]Aspartate and [$^{14}$C]GABA in Rat Hippocampus Slices: Effects of Fatty Acid-Free Bovine Serum Albumin and $CA^{2+}$ Withdrawal", *Brain Research*, 457:205-211 (1988).

Mungall, "Array for Cancer Prognostics", *TRENDS in Biotechnology*, 20(4):144 (2002).

Murphy et al., "Gene Transfer Methods for CNS Organotypic Cultures: A Comparison of Three Nonviral Methods", *Molecular Therapy*, 3(1):113-120 (2001).

Nishizuka et al., "Oligonucleotide Microarray Expression Analysis of Genes Whose Expression Is Correlated with Tumorigenic and Non-Tumorigenic Phenotype of HeLa x Human Fibroblast Hybrid Cells", *Cancer Letters*, 165:201-209 (2001).

Pomeroy et al., "Prediction of Central Nervous System Embryonal Tumour Outcome Based on Gene Expression", *Nature*, 415:436-442 (2002).

Prabhakar et al., "Simultaneous Quantification of Proinflammatory Cytokines in Human Plasma Using the LabMAP™ Assay", *Journal of Immunological Methods*, 260:207-218 (2002).

Schmid et al, "Combinatorial RNAi: A Method for Evaluating the Functions of Gene Families in *Drosophila*", *TRENDS in Neurosciences*, 25(2):71-74 (2002).

Thomas et al., "Quantitative Analysis of Gene Expression in Organotypic Slice-Explant Cultures by Particle-Mediated Gene Transfer", *Journal of Neuroscience Methods*, 84:181-191 (1998).

Van der Meijden et al., "Gene Profiling of Cell Cycle Progression Through S-Phase Reveals Sequential Expression of Genes Required for DNA Replication and Nucleosome Assembly", *Cancer Research*, 62:3233-3243 (2002).

Ziauddin et al., "Microarrays of Cells Expressing Defined cDNAs", *Nature*, 411:107-110 (2001).

* cited by examiner

SEQUENCE LISTING

<160> NUMBER OF SEQ ID NOS: 1

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide; Combined DNA/RNA.
      Nucleotides 20 and 21 are deoxythymidine

<400> SEQUENCE: 1
aacccgccca aguucuccgt t                                              21

METHOD FOR IDENTIFYING GENES THAT ARE UPSTREAM REGULATORS OF OTHER GENES OF INTEREST

CROSS-REFERENCE TO RELATED APPLICATIONS

This applications claims the benefit of priority under 35 U.S.C. Section 119(e) of U.S. Provisional Patent Application No. 60/299,691, filed Jun. 20, 2001, which is incorporated herein by reference.

BACKGROUND OF THE INVENTION

1. Technical Field

The present invention relates to a method of identifying genes based on the gene's function. More specifically, the present invention relates to a device for performing identification of genes that are upstream regulators of the expression of other genes.

2. Description of the Related Art

The Human Genome project led to the elucidation of the sequence of human genes, but the function of many of the genes remains unknown. The current methods of discovering gene function require laborious work and can take months to accomplish. This current approach to the study of gene function is based on the identification of genes whose expression is altered in a disease state, or as a result of a given stimulus. There are cases in which the level of expression of a gene is unaltered, but the gene's function is crucial for a biochemical process associated with a stimulus or a disease. These genes can not be detected by the methods currently used by those of skill in the art. Additionally, the attempt to define drug targets according to changes in levels of expression of genes leads to false negatives because the substrates of many known drugs are proteins that are expressed at constitutive levels. Individuals in the art therefore began to develop alternative methods for determining the function of genes, as are described below.

Alternative methods were developed for inactivating the expression of genes based on knowledge of the gene's sequence. The process of inactivating genes by these methods is referred to as gene silencing. The gene silencing methods can be used to facilitate the functional screening of genes. Two of the methods of silencing genes are the antisense method and RNA interference.

Inactivation of most genes does not lead to visible phenotypic changes in cell cultures expressing those genes. Knowledge about the function of genes whose silencing does not lead to obvious changes in phenotype can be derived from information concerning other genes that have been activated or repressed as a result of silencing a given gene. Important information relating to gene function includes, but is not limited to: (1) data regarding which other genes are regulated by a gene of interest, namely; which genes are activated, induced, or repressed as a result of silencing the gene of interest (i.e., which genes are regulated downstream of the gene of interest); and (2) data regarding which other genes regulate the expression of a given gene of interest (i.e., which genes are upstream regulators of the gene of interest).

Sequitur, Inc, of Natick, Mass., offers a product called "omniscreen." The "omniscreen" method involves inactivating specific genes on high-throughput cell culture disease model screens (phenotypic screens) using a library of antisense compounds targeting thousands of target genes selected on the basis of homology to drugable target gene families. During the process, the Sequitur, Inc., library of antisense targets is used. An alternative method to gene silencing by antisense oligonucleotides, is silencing by RNA interference. For example, in *Caenorhabditis elegans*, the injection of double-stranded RNA (dsRNA) resulted in the specific inactivation of genes containing homologous sequences, a technique termed RNA-mediated interference (RNAi). The same result was found by feeding worms with bacteria that express dsRNA gene (Maeda I. et al.). The term RNAi was coined after the discovery that the injection of dsRNA into *C. elegans* interferes with the expression of specific genes highly homologous in sequence to the delivered dsRNA (Fire A. et al).

Similar approaches to the "omniscreen" method are disclosed in the publications by Schmid et al. Followed by the studies in plants and invertebrates that have showed that the use of dsRNA of approximately 21–25 nucleotides function as key intermediaries in triggering sequence-specific RNA degradation during posttranscriptional gene silencing RNA interference recently the same effect was observed in mammalian cells (Elbashir, S. M. et al. and Caplen N. J. et al, and by Harborth et al.). Both Schmid and Harborth (suggested using RNAi to screen for genes that are essential for cell viability and maintenance of a visible phenotype. The genes were classified based on the impaired cell growth following RNAi.

When combined with microarrays (Pomeroy et al. Mimics K et al, Mungall A J. and Mills J C, et al and Ziauddin J) the above described methods are efficient methods that can be used to identify genes that are regulated by a given gene (i.e., genes that are downstream regulators of the gene of interest). However, there are no high throughput methods that can be used to identify upstream regulators of a given gene. It would therefore be useful to develop a method for high-throughput identification of upstream regulators of a gene. There are also genes whose expression can serve as early markers for diseases and other pathological and physiological processes. It is of particular interest to rapidly identify many genes that are upstream regulators of these genes, and the relationships among these upstream regulators.

SUMMARY OF THE INVENTION

According to the present invention, there is provided a method for identifying genes that regulate the expression of other genes, by placing a viable sample containing genetic material (cells, tissues, organ cultures) in a section of a grid, silencing expression of at least one predetermined gene in the sample, grown in the section of the grid, so that in each section of the grid at least one predetermined gene is silenced, determining the amount of the expression product of a given gene of interest present in each section of the grid, and identifying the sections of the grid in which the silencing was maximal thereby identifying genes that regulate the expression of other genes and the genes of interest identified by the method. Also provided by the present invention is a kit for performing the above method, the kit having a grid for holding a sample, inactivating agents for inactivating genetic material in the sample, and a measuring device for measuring the inactivation of the genetic material.

DESCRIPTION OF THE INVENTION

Generally, the present invention provides a method for the identification of genes that are essential for the maintenance of the level of expression of a given gene of interest More specifically, the present invention provides a method for identifying genes that regulate the amount, activity, phosphorylation, or conformational change of a predetermined protein, group of proteins, RNA of interest, or molecule or material that can be labeled and that is secreted into the medium and the genes identified by the method.

The term "sample" as used herein is intended to include, but is not limited to, cells, any cell line, primary cells, stem cells, embryonic cells and cells obtain from biopsies amniocentesis and CVS tests, tissue slices, organotypic culture, tissue and organ sample both from CNS tissue and non CNS tissue like pancreatic slices, and other biological samples known to those of skill in the art.

The present invention provides a method for the identification of genes that are upstream regulators of a gene or a set of genes of interest. The method includes calorimetric, fluorimetric, and/or radioactive detection of a protein or of an RNA product of the gene(s) of interest or a set of genes of interest, so that changes in the expression of the gene(s) of interest become easily detectable, and can be analyzed by a computer. The method utilizes a grid of samples (i.e., cultured cells or sliced tissue), wherein each section of the grid is treated differently, to silence the expression of at least one gene, other than the gene(s) of interest. Once gene silencing is achieved, the expression of the gene(s) of interest is measured throughout the grid, and genes that affect the levels of the gene(s) of interest are identified. Then, stimuli that are known to increase or decrease the levels of the gene(s) of interest are applied to the cells, and sections of the grid wherein the cells did not respond to the stimuli as expected, are identified. In this way, one can identify, simultaneously, multiple genes that affect the expression of particular gene(s) of interest, and their responsiveness to inducing or repressing external stimuli. Moreover, kinetic study, both as a result of the pre-silencing modifications, during, and post exposure to gene silencing can be obtained by this method. A range of stimulation by a certain component on cells or tissue samples over several intervals of time can be studied, then the same procedure can be utilized to analyze the gene silencing effect.

More specifically, the method generally includes four steps. First, cells are seeded in a multi-well plate, multi-chamber, slides, or any other grids used for growing cells. Alternatively, tissue slices or tissue sample or organ cultures are placed in a grid, and maintained in conditions that enable survival of the slices for several days. Second, the inactivation of genes in the cells or tissues in the grid by any method known in the art is required, so that in each section of the grid, one or more known and predetermined gene(s) is inactivated. Third, 2 to 10 days after the exposure to the specific inactivating agents measurements are taken of the amount of protein or RNA of interest throughout the whole grid. Preferably, the measurement is accomplished using calorimetric and/or fluorimetric and/or radioactive methods. This step can also include the addition of an agent that increases or decreases the level of the protein or RNA of interest. Fourth, sections in the grid wherein the amount of the protein or RNA of interest was either significantly increased or significantly decreased compared to control levels are identified. The gene(s) that were inactivated in these sections are upstream regulators of the protein or RNA of interest.

The method of the present invention also provides the ability of performing kinetic studies. In other words, the method allows one to follow the array at different time intervals and record the development of each grid section. This allows the researcher to not only determine the initial results of the experiments, but also to determine any long-term results of the experiments and having the ability to test the effect of kinetics on the same biological samples (i.e., cells, tissue, culture, primary, slices, etc.) obtained from the same stage of preparation. At this stage there is the ability to add to the medium any compound and or material, for example a cofactor, antagonistagonist, precursor, analog, growth factorr (like EGF, FGF, HGF, NGF), hormone, drug, toxin, and/or oligonucleotide and any compound or material known to those of skill in the art that, at a later step, is assessed as to whether the compound affected the upstream-regulated genes of the certain gene of interest. Each of the above compounds and materials can be either tested separately or in any combination (including pretreatment with one compound/material followed by addition of one or more compounds/materials). Moreover, the effect of conditions on the above can be studied. Example of conditions include, but are not limited to, temperature, gas concentration and composition, and densities of the biological samples (i.e., eukaryotic cells and/or the tissue samples/sections/organ culture).

Different conditions can be tested in parallel, therefore multiple concentrations, durations of time, and combinations can be tested in parallel among sections on grids at the same time. The method also allows for testing from the whole platform of agents and factors on the transcription stage. Additionally, one can also test one or more of the conditions and treatments to compare the treatments at each of the steps of the method. Then one can obtain knowledge as to whether the conditions or the compunds/materials have multistage effects on the genes that effect the genes of interest.

The method of the present invention utilizes a grid of sample (i.e. cells or tissue) wherein each section of the grid is treated to specifically inhibit the expression of one or more predetermined genes, which inhibition is achieved by utilizing sequence information of the gene to be inhibited. Once inhibition of the expression of the gene(s) is achieved, the grid is screened for the desired changes in the expression of a specific gene of interest. The method of the present invention provides use of large-scale specific gene inhibition by use of sequence information in a grid.

The grid of the present invention can be any grid formation known to those of skill in the art. Examples of grids include, but are not limited to, multi-well plates multi inserts, multi-chamber slides, or other cell culture devices that are divisible and able to maintain completely separate compartments.

The sample of cells or tissue are each treated to specifically inhibit the expression of a predetermined gene according to different protocols, using methods known to those of skill in the art. These methods can include, but are not limited to, use of an antisense library based technique, transfection with mutant sequences, application of antisense oligonucleotides or modified stable oligonucleotide derivatives, use of RNAi transfection and other methods known those of skill in the art. Then, the effect of the gene silencing on the expression of a given gene of interest is determined. Each of these methods can be followed by a selection method, that induces or represses the expression of the gene of interest such selection methods are known to those of skill in the art.

The first type of selection methods can be based on the ability of the cells to express the gene of interest under specific culture conditions. For example, this can be basic culture conditions, such that the selection is for growth or survival-essential genes, or for any condition known or shown to effect the expression of the gene of interest.

Alternatively, the selection methods can be in combination with a factor that normally does not cause an induction or repression of the given gene of interest. In this case an alteration can be selected that, only in combination with silencing of a certain gene, is effective in inducing or repressing the expression of the gene of interest.

The second type of selection methods are for the expression of a specific factor that can be measured, and this measurement can be adapted for a selection. This factor can be anything that is accessible to measurement, including but not limited to, secreted molecules, cell surface molecules, soluble and insoluble molecules, binding activities, and activities that induce activities on other cells or induce other organic or inorganic chemical reactions.

The third type of selection methods are for changes in cell structure that are detected by any means that could be adapted for a selection scheme. This includes, but is not limited to, morphological changes that are measured by physical methods such as differential sedimentation, differential light scattering, differential buoyant density, and differential cell volume selected by sieving.

The fourth type of selection methods are based on differences in gene expression that can be directly measured. This includes changes in cell surface markers, changes in biochemical activities, any changes that would be re-selected in changes in binding of fluorescent labeled probes that could be used in conjunction with a Fluorescence Activated Cell Sorter (FACS) or any property that can be used as a basis for a selection.

The fifth type of selection methods are based on differences in gene expression that can be indirectly measured. This includes changes in transcription factor activity that are measured by a synthetic gene construct encoding a selective marker (such as a drug resistance marker or a cell surface marker that could be used in an FACS selection). This category would also include changes in mRNA stability, mRNA localization, and mRNA translation control. All of these changes could be the basis of a selection because a synthetic construct, which is controlled by one of these regulatory events, could be constructed that would drive the expression of an easily selected gene product.

More specifically, the inactivation of gene expression in the second stage can be performed by introduction of antisense DNA or antisense RNA into the sample (cells or tissue). The preferred method for the gene specific inactivation of expression is by introduction of dsRNA molecules into the sample containing the sequence of the gene(s) to be inactivated. This method of inactivation is known in the art as RNA interference (RNAi).

The combination of gene silencing and simultaneous analysis of the expression of multiple genes enables one to identify, in a single experiment, genes that are upstream regulators of many proteins of interest at once, as well as genes that determine the ratio between different proteins or cell markers (reporters) of interest.

Until now, the selection of RNA sequences to be used in RNA interference was made with the intention that the chosen sequence would be specific (Elbashir S M, and Harborth J, Caplen N. J.), and would silence only one target gene. In order for the method disclosed here to be efficient in the screening of the effect of many genes on the expression of the gene(s) of interest, is to use the method in three steps. In step 1, a dsRNA, of not less than 17 bases and not more than 23 bases and whose sequence is identical to more than one gene, is transfected into the cells or tissues so that multiple predetermined genes are silenced. If this leads to a change in the expression of the protein of interest, a second step is performed. In the second step, specific sequences are applied to silence each of the genes silenced in step 1, this time each in a separate section of the grid. Then, in step 3, the places where inhibition or induction take place are identified.

In a preferred embodiment of the invention, a drug that induces or represses the expression of the protein of interest is added during an additional step of the method, step 3, and sections of the grid wherein the induction or inhibition do not take place are identified.

The measurement of the amount of the product of the gene or genes of interest or reporter in the third step is performed by immunocytochemistry or immunofluorescence, using an antibody that specifically recognizes the is protein product of the gene of interest, or a labeled DNA or RNA probe that specifically hybridizes to the RNA product of the gene of interest. The antibody can also recognize a specific conformation of the protein of interest and is able find genes that specifically regulate the desired conformation of a protein of interest. Alternatively, the protein of interest can be a fusion protein of a reporter attached to the gene of interest or to a part of it. This reporter protein has its intrinsic fluorescence or color, and its fluorescence or color is directly measured by fluorimetric or colorimetric method. Fusion proteins with green fluorescent protein, or with luciferase, are examples of products that can be directly and readily determined without immunological reaction or hybridization.

In a specific embodiment of the present invention, there is provided a method that includes pretreatment of the sample with a reporter fluorescent protein linked to a specific promoter. This allows the identification of a grid section based upon the altered levels of fluorescence.

Recently, methods have been developed to measure multiple stimuli simultaneously by fluorimetric methods. (See; e.g., Carson, R. T. and Prabhakar)

The present invention is a genetic method for identifying genes that are essential for the maintenance of specific expression of genes. The method requires that the expression of a specific gene can be positively selected. These identified genes are excellent targets for the development of pharmacological inhibitors that would also act clinically to inhibit the specific gene expression. Thus the present invention provides a gene discovery tool that can effectively identify pharmacological targets for inhibition of deleterious gene expression.

The method of the present invention can be used to address the problem of unusual gene expression patterns, which includes, but is not limited to, cancer. The method is applicable to all aberrant gene expression patterns. The method of the present invention can be used to identify genes that are essential for the growth of cells transformed under general or specific conditions.

To define genes that are essential specifically for transformed cells, a specific gene that differs in expression between the transformed and non transformed cells is identified, and an antisense cDNA or RNAi library is introduced into transformed and non-transformed cells from which the transformed cells were derived, so that each gene is silenced in a different section of a grid. The sections of the grid wherein transformed cells become non transformed, or vice versa, are identified. Alterations specifically absent in the transformed cells, but present in the non-transformed cells, are desired.

The method of the present invention can be used to determine phenotypes related to the release of factors, which includes events that increase or decrease the production of secreted factors, which further includes inflammatory mediators whose release can be modulated. For example, if the production of a specific mediator is necessary for normal immune function but is produced at lethal levels in aberrant situations (such as septic shock), then one can use the production as a screen and look for events that alter or down-regulate productions. In a further embodiment, the selection can be done in the presence of sub-optimal doses of other drugs in order to identify sensitization events.

The method can further be used to determine phenotypes related to changes in cell functions. These selection events are designed to identify genes that are essential for many basic cell functions that depend on any changes that can be externally selected.

The method of the present invention identifies genes of interest identified. The genes identified can be any number of factors or markers. These factors or markers can include, but are not limited to hypoxia-induced factors, apoptosis marker, cancer marker, hypertrophy marker, development marker, metabolism marker including energy production, growth marker, cell division and cell cycle marker, cellular structure marker including cell junction/adhesion, and signal transduction marker including kinases, phosphatases and components of signal. To facilitate tracing changes in gene expression, the gene of interest can be conjugated to a reporter.

The present invention provides a kit for performing the method set forth above. The kit includes a grid for holding a sample, at least one inactivating agent for inactivating genetic material in the sample, examples of such agents are set forth above, and a measuring device for measuring the inactivation of the genetic material. Preferably, the grid is a multi-well plate, a slide, or a similar grid. The measuring device can be, but is not limited to, a colorimetric, fluorometric, or multiplexed fluorescent microsphere immunoassay measuring device. Additionally, the kit can include an analyzing device for analyzing the results.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations that become evident as a result of the teaching provided herein.

EXAMPLES

Methods:

General methods in molecular biology: Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA*, Scientific American Books, New York and in Birren et al (eds) *Genome Analysis: A Laboratory Manual Series*, Vols. 1–4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

RNA Interference by Short Double Stranded RNA.

There are two main strategies for gene silencing using short interfereing RNA sequences: The first is based on the direct transfection of two prehybridized complementary strands of RNA oligonucleotides into the cells, or of oligonucleotides of stable analogs of RNA silencing design dsRNA that is based on a short sequence of nucleotides that are targeted to inhibit sequence specific expression of transcripts (see: Elbashir S. M. et al, 2001; Caplen N. J et al., 2002.and Harborth J. et al., 2002, Dharmacon Technical bulletin 004). The second approach involves the transfection of the cells by a vector that induces the host cells to produce the double strand short RNA molecules that cause the RNA interference (see: Brummelkamp T. R. et al., 2002).

The nucleic acids are introduced into cells or tissues by any one of a variety of known methods within the art (calcium phosphate transfection; electroporation; lipofection; protoplast fusion; polybrene transfection). The host cell can be any eukaryotic cells, which can be transformed with the vector and will support the production of the enzyme. Methods for transformation can be found generally described in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995) and Gilboa, et al. (1986) and include, for example, stable or transient transfection, lipofection, electroporation and infection with recombinant viral vectors. Transfection of tissue can be performed also by the use of the three non viral techniques: lipotransfection, biolistic, and electroporation (in the work of Murphy et al a comparison of these techniques is demonstrated). In another reference (by Thomas A. et al.) the magnitude of the transfection yield was determined based upon immunocytochemical staining for the reporter gene for beta-galatosidase expreression as explored by the application of virus. In addition, see U.S. Pat. No. 4,866,042 for vectors involving the central nervous system and also U.S. Pat. Nos. 5,464,764 and 5,487,992 for positive-negative selection methods.

The following samples were prepared as described for primary cell culture from transfected cells (Minc-Golomb D. 1991), and from CNS and glia cells (Minc-Golomb D. 1994), and tissue slices, CNS and labeling radioactively (Minc-Golomb D. 1988). Organotypic cultures as described by Haas K.; Murphy R. C. and Thomas A.

Cell culture growth and transfection cell and tissue are grown at 37° C. in Dulbecco's modified Eagle medium supplemented with 10% FCS, penicillin and streptomycin. Cells are regularly passaged to maintain exponential growth. Some cell line requires other composition of medium. As recommended in the literatutre, the medium is prepared including the addition of a compund that is required for certain differntiation or growth such as NGF for PC12. Stem cells are use as described by Korbling M. et al. When tissue slices or organotypic culture are used, serum free medium is used in order to reduce glial growth and prevent complications (Murphy R. and Minc Golomb D.). The day before transfection, cells are trypsinized, diluted with fresh medium without antibiotics, and transferred to multi-well plates. Transient transfection of siRNAs is performed using Oligofectamine and OPTIMEM 1 medium (Life Technologies).

The material is first preincubated for 5–10 minutes at room temperature with the Oligofectamine. During the time for this incubation a mixture of OPTIMEM 1 medium siRNA ratio of 0.06 is prepared. The two mixtures are combined and incubated for 20 minutes at room temperature for complex formation. After the addition of OPTIMEM 1 medium to the mixture, the entire mixture is added to the cells in one well resulting in a final concentration of 100 nM for the siRNAs. Cells are usually assayed at least after 40 hours. The assay is usually performed between 40–48 hours after transfection, however in some cases the assay can be perform after a duration of up to 7 days. For transfection, different cells can be used as taught on the Invitrogen web site, where the file of transfection collections is avilable.

Example 1

Cell Line Oriented Gene Grid (CLOGG):

A Combination of Classical Arrays/Expression Profiles and the Gene Inhibition Grid of the Present Invention.

In an approach to focus the research to minimize the resources needed, specific kits were invented that are addressed to specific cell lines (for example for PC12, 3T3, HeLa, HEK 293).

To generate a specific kit for a cell line, the following steps are taken. Genes that are expressed by specific cell lines are identified using standard high microarray experiments. In the case of expressed sequence tags (ESTs), a full length of these cDNAs can be obtained. Antisense clones, antisense oligonucleotides, or double stranded RNA for these genes are used separately in experiments in which this specific cell line is used.

The end product kit is a kit that contains antisense or RNAi sequences for a series of genes that all are expressed by that certain cell line. Included therein are constitutive genes and inducible genes that are inducible when specific conditions are present. This allows individuals to save a lot of resources that are not related to the specific study tested.

Example 2

Identification of Upstream Regulators of the Inducible Nitric Oxide Gene in HeLa Cells.

HeLa cells do not express the inducible nitric oxide gene (iNOS) gene, but can be induced to express it when exposed to lipopolysaccharides and interferon-gamma in the medium.

The method functions by seeding the cells at ~5000 cells/well in minimal essential medium (Life Technologies, Inc., Rockville, Md.), supplemented with 5% calf serum. The cells are allowed to attach. Co-transfection takes place next. The co-transfection occurs with a reporter, a iNOS-luciferase promoter, prepared as described by Gavrilyuk et al. ( ), and with an array of siRNA molecules, each siRNA sequence is in a different well of the 96 well plate.

The array contains a list of known sequences of human genes that have been found in microarray experiments to be constitutively expressed in Hela cells. Data regarding genes that are constitutively expressed in HeLa cells can be obtained from many sources. e.g.: Van Der Meijden et al. and Nishizuka S, et al.

The medium is then changed to minimal essential medium, supplemented with 5% calf serum, containing lipopolysaccharide (LPS, 1 µg/mL), recombinant rat IFN-gamma (20U/mL), or both.

GFP fluorescence is obtained in most wells. Wells that do not show fluorescence are identified.

In the wells containing the siRNA silencing mitogen activator kinase 1 (MAPK1, p38) GFP is not induced. Thus, MAPK is identified as an upstream regulator of the induction of iNOS. The ability to determine whether the factors that change levels are different under the exposure to various gas composition can be determined. This test can be repeated in different conditions, such as hypoxia and septic shock on cells and to find target molecules that can be used to prevent these deleterious processes. Moreover a screen of the effect on different origin of cells and tissue determines the susceptibility/vulnerability of a variety of cells and tissue to these abnormal stages.

The sequence of the siRNA used to silence MAPK is as follows: aa ccucucguac aucggcgag(uu).

Example 3

Identification of Upstream Regulators of Hypoxia-Induced Factor in Endothelial Cells.

Primary human umbilical vein endothelial cells are plated, 5000 cells/well, in basal endothelial cell medium, supplemented with the contents of the bullet kit (Cambrex).

Three days later, siRNAs are added to the wells as described above. Then, cells are immunostained for hypoxia-induced factor-1, (polyclonal antibodies can be purchased from Santa Cruz Biotechnologies). Wells in which HIF showed high levels are identified.

A similar well plate is exposed to hypoxic conditions, so that all of the wells contained therein have high levels of HIF-1. Well that have low levels of HIF-1 are identified in this plate.

Example 4

Identification of Factors that Regulate the Levels of the Phosphorylated Form of BrCa1:

DA-3 cells are seeded in a grid and each section of the grid is transfected with an RNAi sequence that silences a different gene. Four days later, cells are stained with with antibodies against phospho-1457 BrCa1. The section containing the RNAi sequence that silences the gene encoding mre11, aagacaaaaucgaugagguu, is almost deficient in phospho-1457 BrCa1

A Two-Step Analysis of RNAi Screen

In order to screen for a large number of genes using a small number of wells, a two-step approach can be taken. In the first, multiple genes are silenced. The second step takes place only if the first step indicated that at least one of the genes silenced by the RNAi affected the expression of the gene of interest.

Example 5 siRNA Sequence Silencing More than one Gene:

The sequence: aacccgcccaaguucuccg(dTdT) (SEQ ID NO:1) silences all the forms of cytoplasmic myosins, so that the expression of every gene that is affected by the level of any cytoplasmic myosin is expected to be altered in cells transfected with the siRNA of this sequence. At a second stage, specific sequences to each myosin are applied. The kinetic of the effect of butyrate given at variety of concentrations and both with and without an antagonist to a beta adrenergic receptor is tested. Those samples in the grid where gene expression is abolished are compared to the untreated samples for a further study of the effect of the test on cell densities. This test is performed to determine whether these genes are involved in the ability of the cell to use one or more of these energy supply genes when cells are packed or in a relaxed state.

Throughout this application, author and year and patents by number reference various publications, including United States patents. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

REFERENCES

Brummelkamp T R, Bernards R, Agami R, A system for stable expression of short interfering RNAs in mammalian cells. Science. 2002 April 19;296(5567):550–3.

Caplen N J, Parrish S, Imani F, Fire A, Morgan R A, Specific inhibition of gene expression by small double-stranded RNAs in invertebrate and vertebrate systems. Proc Natl Acad Sci U S A. 2001 August 14;98(17):9742–7.

Caplen N J, Taylor J P, Statham V S, Tanaka F, Fire A, Morgan Rescue of polyglutamine-mediated cytotoxicity by double-stranded RNA-mediated RNA interference. Hum Mol Genet. 2002 January 15; 11(2): 175–84

Carson R T, Vignali D A. Simultaneous quantitation of 15 cytokines using a multiplexed flow cytometric assay. J Immunol Methods. 1999;227:41–52.

Culver, 1998. Site-Directed recombination for repair of mutations in the human ADA gene. (Abstract) Antisense DNA & RNA based therapeutics, February, 1998, Coronado, Calif.

Dharmacon Research Inc. RNA oligonucleotide synthesis Technical Bulletin #004 website: See Dharmacon's website. www.dharmon.com Elbashir S M, Harborth J, Weber K, Tuschl T. Analysis of gene function in somatic mammalian cells using small interfering RNAs. Methods. 2002;26: 199–213.

Elbashir S M, Harborth J, Lendeckel W, Yalcin A, Weber K, Tuschl T. Duplexes of 21-nucleotide RNAs mediate RNA interference in cultured mammalian cells. Nature. 2001; 411:494–498.

Fire A, Xu S, Montgomery M K, Kostas S A, Driver S E, Mello C C. Potent and specific genetic interference by double-stranded RNA in *Caenorhabditis elegans*. Nature. 1998 February 19;391 (6669):806–11.

Gilboa, E, Eglitis, M A, Kantoff, P W, Anderson, W F: Transfer and expression of cloned genes using retroviral vectors. BioTechniques 4(6):504–512, 1986.

Gavrilyuk V, Horvath P, Weinberg G, Feinstein D L. A 27-bp region of the inducible nitric oxide synthase promoter regulates expression in glial cells. J Neurochem. 2001; 78:129–140.

Harborth J, Elbashir S M, Bechert K, Tuschl T, Weber K. Identification of essential genes in cultured mammalian cells using small interfering RNAs.J Cell Sci. 2001; 114: 4557–4565.

Huxley et al., The human HPRT gene on a yeast artificial chromosome is functional when transferred to mouse cells by cell fusion", *Genomics,* 9:742–750 (1991).

Kobling M. N. et al. Hepatocytes and Epithelial cells of donor origin in recipients of peripheral blood steam cells Engl J MED Vol 346, No 10: 738–46

Maeda I. Kohara Y, Yamamoto M, Sugimoto A. Large-scale analysis of gene function in *Caenorhabditis elegans* by high-throughput RNAi. Curr Biol. 2001 February 6;11 (3):171–6.

Minc-Golomb D, Eimeral S, Levy Y, Schramm M, Release of D-[3H]aspartate and [14C]GABA in rat hippocampus slices: effects of fatty acid-free bovine serum albumin and Ca2+ withdrawal. Brain Res. 1988 August 9;457(2): 205–11.

Minc-Golomb D, Knobler H, Groner Y, Gene dosage of CuZnSOD and Down's syndrome: diminished prostaglandin synthesis in human trisomy 21, transfected cells and transgenic mice. EMBO J. 1991 August; 10(8): 2119–24.

Minc-Golomb D, Schwartz J P, Expression of both constitutive and inducible nitric oxide synthases in neuronal and astrocyte cultures. Ann N Y Acad Sci. 1994 November 17;738:462–7. Review Murphy R. C. and Messer A. Gene transfer methods for CNS organotypic cultures: a comparison of three nonviral methods Molecular Theraphy 3, 1, 113–121, 2001

Granucci F, Andrews D M, Degli-Esposti M A, Ricciardi-Castagnoli P. IL-2 mediates adjuvant effect of dendritic cells. Trends Immunol. 2002 April 1;23(4): 169–71

Nishizuka S, et al. Oligonucleotide microarray expression analysis of genes whose expression is correlated with tumorigenic and non-tumorigenic phenotype of HeLa x human fibroblast hybrid cells. Cancer Lett. 2001 April 26;165(2):201–9.

Nishizuka S, et al. Oligonucleotide microarray expression analysis of genes whose expressionis correlated with tumorigenic and non-tumorigenic phenotype of HeLa x human fibroblast hybrid cells. Cancer Lett. 2001 April 26;165(2):201–9.

Prabhakar U, Eirikis E, Davis H M. Simultaneous quantification of proinflammatory cytokines in human plasma using the LabMAP assay. J Immunol Methods. 2002; 260: 207–218.

Schmid A, Schindelholz B, Zinn K. Combinatorial RNAi: a method for evaluating the functions of gene families in Drosophila.Trends Neurosci. 2002;25:71–74.

Thomas A., et al. Quantitative analysis of gene expression in organotypic cultures by particle-mediated gene transfer. J. Neurosci Meth 84,181–191, 1998

Van Der Meijden C M, et al., Gene Profiling of Cell Cycle Progression through S-Phase Reveals Sequential Expression of Genes Required for DNA Replication and Nucleosome Assembly, Cancer Res 2002 June 1;62(11):3233–43

Ziauddin J, Sabatini D M. Microarrays of cells expressing defined cDNAs. Nature. 2001 May 3;411(6833):107–10.

Pomeroy S L, et al. Prediction of central nervous system embryonal tumour outcome based on gene expression. Nature. 2002 January 24;415(6870):436–42.

Mimics K, Middleton F A, Lewis D A, Levitt P. Analysis of complex brain disorders with gene expression microarrays: schizophrenia as a disease of the synapse. Trends Neurosci. 2001 August;24(8):479–86. Review.

Mungall A J. Array for cancer prognostics. Trends Biotechnol. 2002 April;20(4): 144.
Mills J C, Roth K A, Cagan R L, Gordon J I. DNA microarrays and beyond: completing the journey from tissue to cell. Nat Cell Biol. 2001 August;3(8):E175
Patents:
20020048814 Models for gene silencing using poly-dTsequence Oeller Paul
U.S. Pat. No. 6,025,192 Modified retroviral vectors Beach, et al.
U.S. Pat. No. 6,255,071 Mammalian viral vectors and their uses Beach, et al.
20020006664 Arrayed transfection method and uses related thereto Sabatini D. M.
20020022029 Human RRP sequences and methods of use Lioubin M. N. et al.
U.S. Pat. No. 6,326,193 Insect control agent Liu, et al.
2002003846 Methods for screening and identifying host pathogn defense genes Ausubel F. M. et al.

What is claimed is:

1. A method for identifying a regulator gene that regulates the expression of a pre-selected gene of interest, comprising the steps of: placing a sample containing genetic material in a grid having multiple sections, wherein the genetic material comprises the pre-selected gene of interest and at least one predetermined gene;
   silencing expression of at least one predetermined gene in the sample, wherein at least one predetermined gene is silenced in each section of the grid and in multiple sections of the grid, different predetermined genes are silenced;
   determining the level of expression of the pre-selected gene of interest for each section of the grid after the predetermined gene is silenced;
   identifying the sections of the grid in which the expression of the pre-selected gene of interest is increased or decreased as compared to a control; and
   recognizing the revealed predetermined gene of those sections of the grid wherein the expression of the pre-selected gene of interest is increased or decreased as a regulator gene of the pre-selected gene of interest.

2. The method according to claim 1, wherein the sample further comprises a reporter system that produces a colorimetric, fluorimetric or radioactive signal indicative of the level of expression of the gene-of interest in a section of the grid.

3. The method according to claim 2, wherein the step of determining the level of expression includes using a method selected from the group consisting of: fluorimetric, colorimetric, and radioactive methods.

4. The method according to claim 1, further comprising the step of measuring expression of the gene of interest of sections of the grid at various time intervals.

5. The method according to claim 1, further comprising adding a compound selected from the group consisting of: a cofactor, antagonist, agonist, precursor, analog, growth factor, hormone, drug, toxin, and oligonucleotide to test the affect of the compound on the regulator gene.

6. The method according to claim 5, further comprising measuring whether the compound has an affect on the regulator gene when a condition is added that changes over time or between samples, wherein the condition is selected from the group consisting of: temperature changes, gas concentration changes, gas composition changes, and changes in the density of the sample.

7. The method according to claim 5, further comprising testing the affect of the compound using a platform of agents and factors.

8. The method according to claim 6, further comprising comparing the effects of the condition on the regulator gene at different time intervals.

9. The method of claim 1, wherein at least two predetermined genes are silenced in each section of the grid and the sample comprises cells or tissue.

10. The method of claim 1, wherein the grid is selected from the group consisting of: a multi-well plate and a slide, and a different predetermined gene is silenced in each section of the grid.

11. A method for identifying a regulatory gene that regulates the expression of a pre-selected gene of interest, the method comprising the steps of:
   placing a sample in a section of a grid wherein the sample comprises genetic material comprising the pre-selected gene of interest and more than three predetermined genes;
   silencing the expression of predetermined genes in the sample, whereby in each section of the grid more than three predetermined genes are silenced;
   determining the amount of at least one protein of interest or RNA of interest from the pre-selected gene of interest in each section of the grid;
   identifying the sections in the grid wherein a change in the amount of the protein or the RNA is present as compared to a control;

placing the sample on a second grid;
silencing each of the predetermined genes in the identified sections of the grid individually, in different sections of the second grid;
identifying the sections in the second grid in which the expression of the protein or RNA is increased or decreased as compared to a control and
recognizing the revealed predetermined gene silenced in a particular section of the grid, wherein the expression of the protein or RNA is increased or decreased as a regulator gene of the pre-selected gene of interest.

12. The method according to claim 11, wherein said silencing step is accomplished by transfection with a double stranded RNA oligonucleotide between 16 and 21 bases in length.

13. The method according to claim 11, wherein the sample further one or more colorimetric or fluorimetric or radioactive signals indicative of the level of expression of the gene of interest in a section of a grid.

14. The method according to claim 11, wherein the identifying step comprises staining each section of the grid for a phospho-protein.

15. The method of claim 11, wherein the sample comprises cells or tissue, and the predetermined gene is silenced by using a sequence that is designed based on conserved sequence of a gene family or by using a mixture of RNAi molecules that each are specific to different predetermined genes.

* * * * *